United States Patent
Ahn

(10) Patent No.: US 10,845,347 B2
(45) Date of Patent: Nov. 24, 2020

(54) PARTICLE SAMPLING PROBE AND FINE DUST MEASURING DEVICE USING SAME

(71) Applicant: INDUSTRY-UNIVERSITY COOPERATION FOUNDATION HANYANG UNIVERSITY ERICA CAMPUS, Ansan-si (KR)

(72) Inventor: Kang Ho Ahn, Seoul (KR)

(73) Assignee: INDUSTRY-UNIVERSITY COOPERATION FOUNDATION HANYANG UNIVERSITY ERICA CAMPUS

( * ) Notice: Subject to any disclaimer, the term of this patent is extended or adjusted under 35 U.S.C. 154(b) by 201 days.

(21) Appl. No.: 15/762,185

(22) PCT Filed: Sep. 7, 2016

(86) PCT No.: PCT/KR2016/010032
§ 371 (c)(1),
(2) Date: Jun. 26, 2018

(87) PCT Pub. No.: WO2017/052116
PCT Pub. Date: Mar. 30, 2017

(65) Prior Publication Data
US 2018/0348096 A1 Dec. 6, 2018

(30) Foreign Application Priority Data
Aug. 5, 2016 (KR) .................. 10-2016-0100312

(51) Int. Cl.
*G01N 33/00* (2006.01)
*G01N 1/24* (2006.01)
*G01N 15/06* (2006.01)
*G01N 1/22* (2006.01)
G01N 15/00 (2006.01)
G01N 1/38 (2006.01)

(52) U.S. Cl.
CPC ....... *G01N 33/0009* (2013.01); *G01N 1/2273* (2013.01); *G01N 1/24* (2013.01);
(Continued)

(58) Field of Classification Search
CPC ...... G01N 1/2247; G01N 1/24; G01N 1/2273; G01N 15/06; G01N 33/0009;
(Continued)

(56) References Cited

U.S. PATENT DOCUMENTS

| 4,942,774 A | 7/1990 | McFarland |
| 8,567,266 B2 | 10/2013 | Kaminski |

(Continued)

FOREIGN PATENT DOCUMENTS

| CN | 103091132 A | 5/2013 |
| CN | 203133287 U | 8/2013 |

(Continued)

OTHER PUBLICATIONS

International Search Report (in English and Korean) and Written Opinion (in Korean) issued in PCT/KR2016/010032, dated Jan. 31, 2017; ISA/KR.

*Primary Examiner* — Benjamin R Schmitt
(74) *Attorney, Agent, or Firm* — Harness, Dickey & Pierce, P.L.C.

(57) ABSTRACT

The present invention relates to a dust measuring apparatus and, more particularly, to a miniaturized fine dust measuring apparatus. According to one embodiment of the present invention, a non-sampling fluid is discharged irrespective of a speed change of an external fluid, thereby providing a particle sampling probe and a miniaturized fine dust measurement apparatus that provide uniform-speed sampling. Accordingly, it is possible to eliminate a restriction on a place for fine dust measurement.

6 Claims, 15 Drawing Sheets

(52) U.S. Cl.
CPC ............... *G01N 15/06* (2013.01); *G01N 1/38* (2013.01); *G01N 2001/2279* (2013.01); *G01N 2001/2285* (2013.01); *G01N 2015/0046* (2013.01)

(58) Field of Classification Search
CPC ..... G01N 2001/225; G01N 2001/2285; G01N 2001/2279; G01N 2015/0046; G01N 33/0004
USPC ...... 73/28.01, 31.05, 863.41, 863.51, 864.73
See application file for complete search history.

(56) References Cited

U.S. PATENT DOCUMENTS

2011/0203931 A1* 8/2011 Novosselov ......... G01N 1/2202
204/600

| | | |
|---|---|---|
| 2013/0047704 A1 | 2/2013 | Bae et al. |
| 2014/0130615 A1 | 5/2014 | Karki |

FOREIGN PATENT DOCUMENTS

| | | |
|---|---|---|
| CN | 204085969 U | 1/2015 |
| JP | 2005-024409 A | 1/2005 |
| JP | 2013-217821 A | 10/2013 |
| KR | 2004-0095087 A | 11/2004 |
| KR | 2009-0003021 A | 1/2009 |
| KR | 2010-0041579 A | 4/2010 |
| KR | 101031612 B1 | 4/2011 |
| KR | 2012-0071816 A | 7/2012 |
| KR | 2013-0001594 A | 1/2013 |
| KR | 10-1311426 B1 | 9/2013 |
| KR | 2014-0114927 A | 9/2014 |
| KR | 10-1490324 B1 | 2/2015 |

\* cited by examiner

PARTICLE SAMPLING PROBE AND FINE DUST MEASURING DEVICE USING SAME

TECHNICAL FIELD

The present disclosure relates to a dust measuring device, and more particularly, to a miniaturized fine dust measuring device.

BACKGROUND ART

It is very important to accurately measure the mass or size distribution of particles (dusts) in the atmosphere because it is closely related to the atmospheric environment, indoor environment, working environment, or the like that affects human health. Generally, in order to accurately measure the mass or size distribution of particles, a large stationary fine particle measuring device is used. However, it is necessary to measure fine dusts at various positions and altitudes in order to grasp the distribution and movement route of the fine dusts. However, since it is impossible to move the stationary fine dust measuring device, it is necessary to install the fine dust measuring device at every point to be measured. However, there is a problem in that it is impossible to measure fine dusts at a high altitude, in addition to the problems of cost, space, and the like.

Meanwhile, when the fine dust measuring device is intended to measure fine dusts while moving, it is difficult to accurately measure the mass or size distribution of the particles because the direction and speed of the airflow to be introduced fluctuates greatly. In order to measure the exact mass or size distribution of particles, it is necessary for a sampler to accurately sample particles in the atmosphere and to send the sampled particles to a measurement instrument without loss. Sampling the particles in the atmosphere as they are in this way is called isokinetic sampling (constant-speed sampling). That is, it is difficult to perform constant-speed sampling because there is a relative speed between the air to be sampled during movement and the fine dust measuring device.

DETAILED DESCRIPTION OF THE INVENTION

Technical Problem

The present disclosure provides a particle sampling probe that maintains constant-speed sampling conditions by itself.

The present disclosure provides a particle sampling probe that provides mechanical feedback with a high response rate.

The present disclosure provides a miniaturized fine dust measuring device by mounting a miniaturized particle sampling probe.

The present disclosure provides a fine dust measuring device capable of measuring a normal fine dust concentration in a low air pressure region.

The present disclosure provides a fine dust measuring device that normally operates even when the altitude of a flying object detachably attached to a balloon changes.

Technical Solution

According to an aspect of the present disclosure, there is provided a particle sampling probe.

The particle sampling probe according to one embodiment of the present disclosure may include: an external duct extending in a longitudinal direction and including a first inlet into which an external fluid is introduced and a first outlet provided at an end opposite the first inlet; and a sampling duct extending in the longitudinal direction inside the external duct and including a second inlet into which a sampling fluid in the external fluid is introduced, and a second outlet provided at an end opposite the second inlet. The outflow direction of the first outlet may be formed to be at least partially opposite the inflow direction in which the external fluid is introduced into the first inlet.

According to one embodiment of the present disclosure, the outflow direction of the first outlet may face the inflow direction in which the external fluid is introduced into the first inlet.

According to one embodiment of the present disclosure, the external duct may include a discharge passage between the first inlet and the first outlet such that a non-sampling fluid in the external fluid flows in a direction that faces the inflow direction of the first inlet.

According to one embodiment of the present disclosure, the first outlet may be formed to be spaced apart from the first inlet in the longitudinal direction.

According to one embodiment of the present disclosure, the outflow direction of the first outlet may form an acute angle with the inflow direction in which the external fluid is introduced into the first inlet.

According to one embodiment of the present disclosure, the sampling duct and the external duct may be coaxial to each other.

According to one embodiment of the present disclosure, between the sampling duct and the external duct, there may be provided a gap in which the non-sampling fluid in the external fluid flows.

The particle sampling probe according to one embodiment of the present disclosure may include: a first external duct extending in a longitudinal direction and including a first sub-inlet into which an external fluid is introduced and a first sub-outlet provided at an end opposite the first sub-inlet; a second external duct extending in a longitudinal direction inside the first external duct and including a second sub-inlet into which a part of the external fluid is introduced and a second sub-outlet provided at an end opposite the second sub-inlet; and a sampling duct extending in the longitudinal direction inside the second external duct and including a second inlet into which a sampling fluid in the fluid introduced into the second sub-inlet is introduced, and a second outlet provided at an end opposite the second inlet. An outflow direction of the first and second-sub outlets may be formed to be at least partially opposite an inflow direction in which the external fluid is introduced into the first sub-inlet.

According to one embodiment of the present disclosure, the outflow direction of the first and second sub-outlet may form an acute angle with the inflow direction in which the external fluid is introduced into the first sub-inlet.

According to one embodiment of the present disclosure, the first sub-outlet may be formed in the first external duct to be spaced apart from the first sub-inlet in the longitudinal direction, and the second sub-outlet may be formed in the second external duct to be spaced apart from the second sub-inlet in the longitudinal direction.

According to one embodiment of the present disclosure, an outer wall of the first external duct and an outer wall of the second external duct may provide a continuous stream line for the external fluid.

According to one embodiment of the present disclosure, an outer wall of the first external duct and an outer wall of the second external duct may provide a discontinuous stream line for the external fluid.

According to an aspect of the present disclosure, there is provided a fine dust measuring device.

The fine dust measuring device according to one embodiment of the present disclosure may include: a particle sampling probe configured to sample an introduced external fluid at a constant speed and to discharge a sampling fluid; a flow rate control pump configured to receive the sampling fluid discharged by the particle sampling probe through a main flow path and to discharge the sampling fluid to an outside; a sensor configured to receive a part of the sampling fluid introduced from the main flow path and to measure a concentration of fine dusts; and a processor configured to receive the concentration of the fine dusts from the sensor and to generate fine dust measuring information having the concentration of the fine dusts.

According to one embodiment of the present disclosure, the particle sampling probe may include: an external duct extending in a longitudinal direction and including a first inlet into which an external fluid is introduced and a first outlet provided at an end opposite the first inlet; and a sampling duct extending in the longitudinal direction inside the external duct and including a second inlet into which a sampling fluid in the external fluid is introduced, and a second outlet provided at an end opposite the second inlet. The outflow direction of the first outlet may be formed to be at least partially opposite the inflow direction in which the external fluid is introduced into the first inlet.

According to one embodiment of the present disclosure, The fine dust measuring device may further include a conditioner configured to heat the sampling fluid discharged by the particle sampling probe to a predetermined temperature or to filter particles which is equal to or larger than a predetermined size among the fine dust particles included in the sampling fluid, and to discharge the sampling fluid to the main flow path.

Advantageous Effects

According to one embodiment of the present disclosure, it is possible to provide a particle sampling probe that provides constant-speed sampling by ejecting a non-sampling fluid irrespective of the speed change of an external fluid.

According to one embodiment of the present disclosure, by providing a miniaturized fine dust measuring device, it is possible to eliminate restrictions on a place where fine dust measurement is to be performed.

According to one embodiment of the present disclosure, it is possible to measure fine dusts in real time during movement using a miniaturized fine dust measuring device.

According to one embodiment of the present disclosure, it is possible to accurately measure the concentration of fine dusts even at a low atmospheric pressure.

According to one embodiment of the present disclosure, after reaching a high altitude while consuming a small amount of energy by using a balloon, the fine dust measuring device can measure the concentration of fine dusts for a long time while moving through a flight vehicle.

According to one embodiment of the present disclosure, it is possible to prevent a measurement error from occurring even when the posture of the flight vehicle detachably attached to the balloon is changed.

MODE FOR CARRYING OUT THE INVENTION

Figure 1:
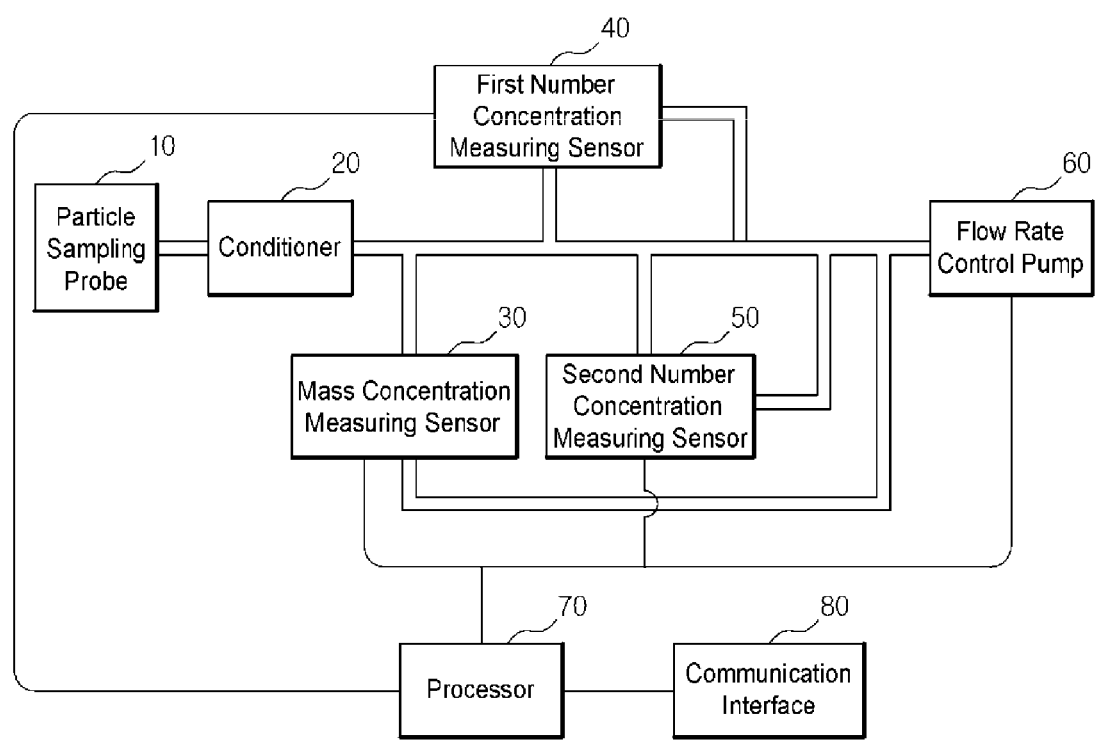
FIG. 1 is a block diagram of a fine dust measuring device according to an embodiment of the present disclosure.

The present disclosure may be variously modified and may have various embodiments. Thus, specific embodiments are illustrated in the drawings and described in detail through the detailed description. However, it is to be understood that this is not intended to limit the present disclosure to the specific embodiments, but all the modifications, equivalents, and substitutions fall within the spirit and scope of the present disclosure. In addition, in this specification, when it is described that one constituent element "transmits" a signal to another constituent element, it should be understood that although the one constituent element may be directly connected to the other constituent element so as to transmit the signal, the signal may be transmitted via still another constituent element interposed therebetween.

FIG. 1 is a diagram exemplifying a fine dust measuring device according to an embodiment of the present disclosure.

Referring to FIG. 1, a fine dust measuring device 5 according to an embodiment of the present disclosure includes a particle sampling probe 10, a conditioner 20, a mass concentration measuring sensor 30, a first number concentration measuring sensor 40, a second number concentration measuring sensor 50, a flow rate control pump 60, a flow rate control sensor 62, an atmospheric pressure sensor 64, a processor 70, a memory 72, and a communication interface 80.

The particle sampling probe 10 ejects a sampling fluid irrespective of the speed change of the external fluid to as to cause a sampling water with a predetermined flow rate to flow into the conditioner 20 or the mass concentration measuring sensor 30, the first number concentration measuring sensor 40, and the second number concentration measuring sensor 50. The particle sampling probe 10 includes an external duct extending in a longitudinal direction and including a first inlet into which the external fluid flows and a first outlet provided at an end opposite the first inlet, and a sampling duct extending in a longitudinal direction inside the external duct and a second inlet into which the sampling fluid of the external fluid flows and a second outlet provided at an end opposite the second inlet. The outflow direction of the first outlet is formed to be at least partially opposite the inflow direction in which the external fluid flows into the first inlet. The detailed structure and operation principle of the particle sampling probe 10 will be described in detail later with reference to FIGS. 3 to 7.

The conditioner 20 may include a heater for raising the temperature of the sampling fluid introduced from the particle sampling probe 10 by a specified reference value and a cyclone or an impactor configured to remove particles included in the sampling fluid and having a size larger than a specified size. Therefore, the conditioner 20 may raise the temperature of the sampling fluid by a reference value, may remove particles included in the sampling fluid and having a size larger than the specified size, and may then provide the sampling fluid to the mass density measuring sensor 30, the first number concentration measuring sensor 40, and the second number concentration measuring sensor 50. At this time, the conditioner 20 may be excluded from the fine dust measuring device depending on an implementation method, and the particle sampling probe 10 may provide the sampling fluid to the mass concentration measuring sensor 30, the first number concentration measuring sensor 40, and the second number concentration measuring sensor 50. At this time, a main flow path, through which the sampling fluid flows from the conditioner 20 to the flow rate control pump 60, may be formed, and an inflow path, through which the sampling fluid flows from the particle sampling probe 10 to the conditioner, may be formed. Alternatively, when the conditioner 20 is omitted depending on an implementation method, a main flow path, through which the sampling fluid flows from the particle sampling probe 10 to the flow rate control pump 60, may be formed.

The mass concentration measuring sensor 30 measures the mass concentration of the fine dusts contained in the sampling fluid flowing thereinto from the main flow path. The mass concentration measuring sensor 30 transmits the mass concentration to the processor 70. For example, the mass concentration measuring sensor 30 may be a sensor configured to measure the mass of fine dusts in the impactor or the like. The mass concentration measuring sensor 30 includes a pump and may allow a part of the sampling fluid to flow into the mass concentration measuring sensor 30 from the main flow path through the operation of the pump.

The first number concentration measuring sensor 40 measures the number concentration of the fine dusts contained in the sampling fluid flowing thereinto from the main flow path. The first number concentration measuring sensor 40 may measure the number concentration of fine dusts contained in the sampling fluid flowing thereinto through an optical measuring method. The first number concentration measuring sensor 40 includes a pump and may allow a part of the sampling fluid to flow into the first number concentration measuring sensor 40 from the main flow path through the operation of the pump. Since the first number concentration measuring sensor 40 measures the number concentration of the fine dusts through the optical measuring method, the number concentration measuring sensor 40 may measure the number concentration for each particle diameter (e.g., the number concentration of fine dusts having respective particle diameters corresponding to 0.3 to 5.0 μm) by measuring fine dusts corresponding to relatively large particle compared with the second number concentration measuring sensor 50. The first number concentration measuring sensor 40 transmits the number concentration for each particle diameter to the processor 70. For example, the first number concentration measuring sensor 40 may be a sensor configured to measure the number concentration of fine dusts for each diameter, such as an Optical Particle Counter (OPC) or the like.

The second number concentration measuring sensor 50 measures the number concentration of the fine dusts contained in the sampling fluid flowing thereinto from the main flow path. The second water concentration measuring sensor 50 measures the concentration of fine dusts by causing the sampling fluid to pass through a volatile solution phase so as to cause the volatile solution to be condensed and sensing the volatile solution condensed on the fine dusts. Therefore, the second number concentration measuring sensor 50 may measure the number concentration of the fine dusts corresponding to the relatively small particles compared with the first number concentration measuring sensor 40. The second number concentration measuring sensor 50 includes a pump and may allow a part of the sampling fluid to flow into the second number concentration measuring sensor 50 from the main flow path through the operation of the pump. The second number concentration measuring sensor 50 transmits the number concentration to the processor 70. For example, the second number concentration measuring sensor 50 may be a sensor configured to measure the number concentration of fine dusts, such as an Condensation Particle Counter (CPC) or the like.

The flow rate control pump 60 adjusts the flow rate per unit time flowing thereinto from the particle sampling probe 10 to a specified value. That is, the flow rate control pump 60 may be connected to the particle sampling probe 10 or the conditioner 20 through the main flow path and may adjust the flow rate per unit time of the sampling fluid that is suctioned from the main flow path and discharged to the outside, so that the flow rate per unit time of the sampling fluid discharged by the particle sampling probe 10 can be adjusted. At this time, the flow rate control pump 60 may be adjusted so as to discharge a flow rate larger than the sum of the flow rates suctioned by respective sensors 30, 40, and 50.

The flow rate control sensor 62 generates sensor values including an atmospheric pressure difference between an internal atmospheric pressure and an external atmospheric pressure of the fine dust measuring device or a mass flow rate of the sampling fluid through a differential pressure sensor or a mass flow rate sensor, and transmits the generated sensor values to the processor 70.

The atmospheric pressure sensor 64 measures the atmospheric pressure around the fine dust measuring device 5 and transmits the measured atmospheric pressure to the processor 70.

The processor 70 receives the mass concentration, the number concentration of each particle diameter, and the number concentration from the above-described components, and generates fine dust measurement information including the received mass concentration, number concentration of each particle diameter, and the number concentration. The processor 70 transmits the fine dust measurement information to an external device via the communication interface 80. In addition, the processor 70 may check a target sensor value according to the atmospheric pressure and may control the flow rate control pump 60 so as to control the flow rate per unit time of the sampling fluid such that the sensor value output from the flow rate control sensor 62 becomes the target sensor value. At this time, the memory 72 stores flow control information including respective atmospheric pressures and sensor values to match each other, and the processor 70 may check the target sensor value according to the current atmospheric pressure by checking the flow control information.

The communication interface 80 is connected to an external device through a known communication method (for example, wired communication, RF communication, ultrasonic communication, or the like) and transmits fine dust measurement information to the external device.

The fine dust measuring device 5 has been described above as including a mass concentration measuring sensor 30, a first number concentration measuring sensor 40, and a second number concentration measuring sensor 50 with reference to FIG. 1. However, the mass concentration measuring sensor 30 and the first number concentration measuring sensor 40 may be omitted in the fine dust measuring device depending on the implementation method of the fine dust measuring device.

Figure 2:
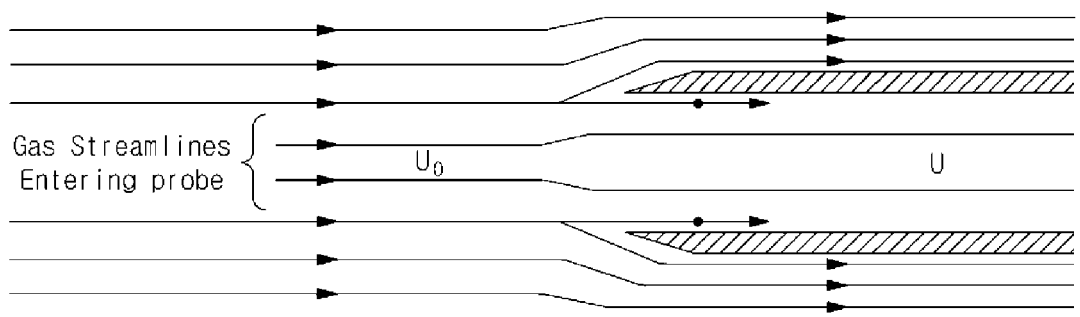
FIG. 2 is a diagram exemplifying oversampling and undersampling occurring during sampling by a sampling probe.
Figure 2:
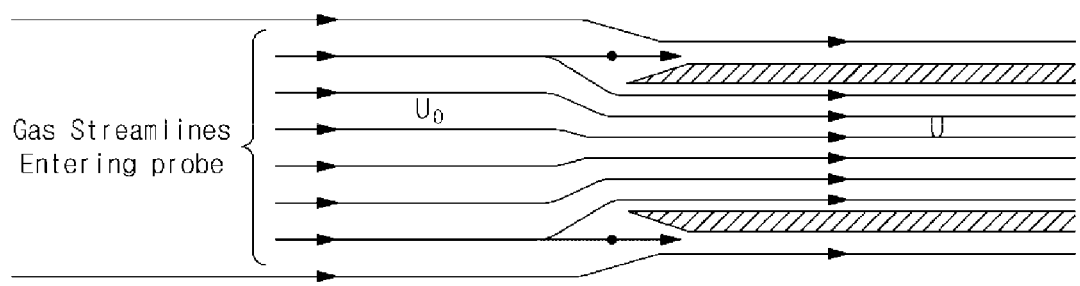

FIG. 2 is a diagram illustrating oversampling and undersampling occurring during sampling by a sampling probe.

When the constant speed sampling is not performed on the external fluid, an oversampling or undersampling problem occurs. Oversampling occurs when a suctioned air flow rate is faster than a probe flow rate as in case 93 in FIG. 2, and undersampling occurs when the speed of the suctioned air flow is slower than the probe flow speed, as indicated in case 96 in FIG. 2. When oversampling or undersampling occurs in this way, the particles, the concentration of which is higher or smaller than the concentration of the particles in the air, are sampled. In this case, even if an attempt is made to perform an accurate measurement using the measuring device, it is impossible to know the exact concentration of the particles due to sampling error. In particular, it is very difficult to perform constant-speed sampling when the flow rate around the sampling probe is not constant.

A fine dust measuring device according to an embodiment of the present disclosure includes a particle sampling probe capable of constant-speed sampling without being affected by a change in external air flow. Hereinafter, a particle sampling probe according to an embodiment of the present disclosure will be described with reference to FIGS. 3 to 7.

Figure 3:
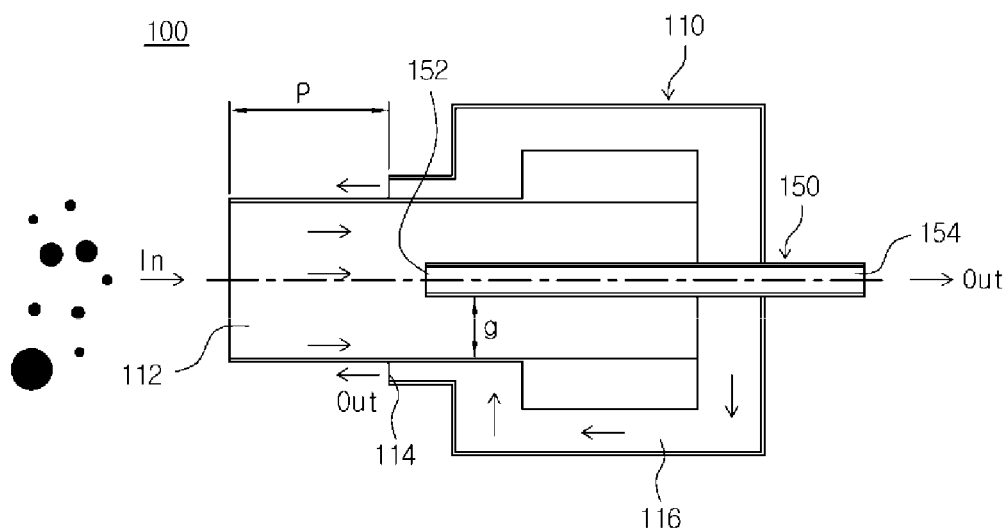
FIG. 3 illustrates a cross-sectional view and a partially cut-away perspective view for explaining a particle sampling probe according to a first embodiment of the present disclosure.
Figure 3:
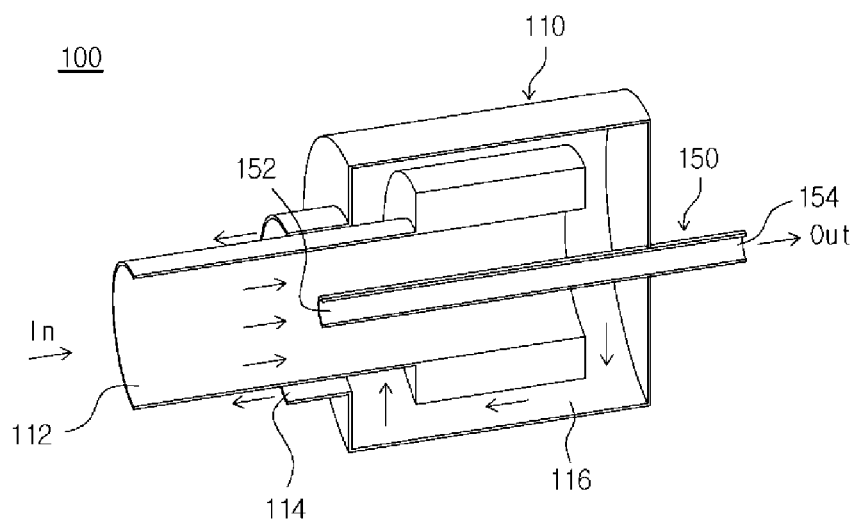

FIG. 3 illustrates a cross-sectional view and a partially cut-away perspective view for explaining a particle sampling probe according to a first embodiment of the present disclosure.

Referring to FIG. 3, the particle sampling probe 100 according to a first embodiment of the present disclosure may include an external duct 110 and a sampling duct 150. Hereinafter, each configuration will be described in detail.

The external duct 110 may extend in the longitudinal direction and may include a first inlet 112 into which an external fluid is introduced and a first outlet 114 provided in an end opposite the first inlet 112. Here, the first outlet 114 may be located in an end portion opposite the first inlet 112 or in the end portion of the lateral surface of the first inlet 112.

The first inlet 112 may receive the external fluid to be sampled. A part of the external fluid introduced into the first inlet 112 may be provided to the sampling duct 150 to be described later and the rest of the introduced external fluid may be discharged through the first outlet 114 to be described later.

The first outlet 114 may discharge the remaining fluid other than the fluid to be sampled. At this time, the outflow direction of the first outlet 114 may be formed to be at least partially opposite the inflow direction in which the external fluid is introduced into the first inlet 112. More specifically, the outflow direction of the first outlet 114 may be formed to be at least partially opposite the inflow direction of the first inlet 112.

In addition, the first outlet 114 may be spaced apart from the first inlet 112 by a distance p in the longitudinal direction. At this time, the spaced distance p may be a natural number larger than 0. This is a configuration for constant-speed sampling, and a detailed description thereof will be given later.

The external duct 110 may further include a discharge passage 116 between the first inlet 112 and the first outlet 114. The discharge passage may be configured to allow the non-sampling fluid to flow in a direction facing the inflow direction of the first inlet 112.

The sampling duct 150 may extend in a direction substantially the same as the external duct 110 and may be provided inside the external duct 110. More specifically, the outer wall of the sampling duct 150 may be spaced apart from the inner wall of the external duct 110 by a distance g. Also, the sampling duct 150 may be coaxial with the external duct 110.

The sampling duct 150 may include a second inlet 152 into which the sampling fluid in the external fluid is introduced and a second outlet 154 provided at the end opposite the second inlet.

The second inlet 152 of the sampling duct 150 may be provided with a part of the external fluid introduced into the first inlet 112 of the external duct 110 as a sampling fluid. In this case, since the sampling duct 150 is spaced apart from the external duct 110 by a distance g, the second inlet 152 of the sampling duct 150 may be selectively provided with a central fluid in the external air introduced into the first inlet 112 of the external duct 110.

Meanwhile, the non-sampling fluid which was not able to be introduced into the second inlet 152 of the sampling duct 150 flows through a gap g between the outer wall of the sampling duct 150 and the inner wall of the external duct 110. Accordingly, the non-sampling fluid can be supplied to the discharge passage 116 described above.

The fluid introduced into the second inlet 152 of the sampling duct 150 may be transferred to a measurement instrument through the second outlet 154 provided in the end opposite the second inlet 152. At this time, the end opposite the second inlet 152 may be directly or indirectly connected to the measurement instrument.

Hereinafter, a method of operating the particle sampling probe according to the first embodiment of the present disclosure will be described.

The fluid containing particles to be measured may be provided through the first inlet 112 of the external duct 110. The fluid introduced into the first inlet 112 is directed to the first inlet 152 and the first outlet 114 of the sampling duct 150.

At this time, the fluid introduced into the first inlet 152 of the sampling duct 150 flows through the center of the external duct 110 and may be insensitive to a change in the speed of the external air. Accordingly, the fluid introduced into the first inlet 152 of the sampling duct 150 may be subjected to a constant-speed sampling measurement.

Alternatively, the fluid directed to the first outlet 114 of the external fluid flows along the edge of the external duct 110 and may cause oversampling or undersampling. Therefore, by discharging the noise inducing fluid flowing along the edge of the external duct 110, the sampling accuracy can be improved.

The fluid directed toward the first outlet 114 of the external fluid may flow in the direction facing the first inlet 112 by passing through the discharge passage 116.

The fluid that has passed through the discharge passage 116 may be ejected through the first outlet 114. At this time, the non-sampling fluid may be ejected in a direction facing the first inlet 112.

According to the particle sampling probe of the first embodiment of the present disclosure, the first inlet 112 and the first outlet 114 are spaced apart from each other by a distance p in the longitudinal direction of the outer duct 110. At this time, p may be a natural number larger than 0. Accordingly, when the external fluid flows along the outer wall of the external duct 110 to the first outlet 114 through the first inlet 112, a pressure drop occurs due to the flow interface due to the spaced distance p. Accordingly, the pressure of the external fluid at the first inlet 112 becomes higher than the pressure of the external fluid at the first outlet 114. This may mean that the pressure of the first outlet 114 is kept lower than the pressure of the first inlet 112 even when the speed profile of the external fluid changes. As a result, even when the speed of the external fluid changes, the sampling duct 150 can perform the constant-speed sampling by discharging the non-sampling fluid through the first outlet 114.

In addition, since a mechanical operation is performed in response to the change in the flow rate of the external fluid, the outflow speed at the outlet can be automatically adjusted at a high response speed.

Figure 4:
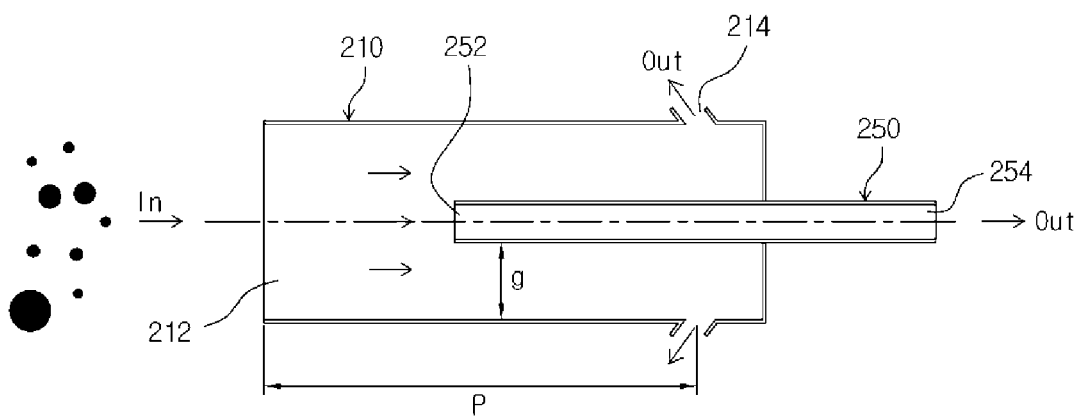
FIG. 4 illustrates a cross-sectional view and a partially cut-away perspective view for explaining a particle sampling probe according to a second embodiment of the present disclosure.
Figure 4:
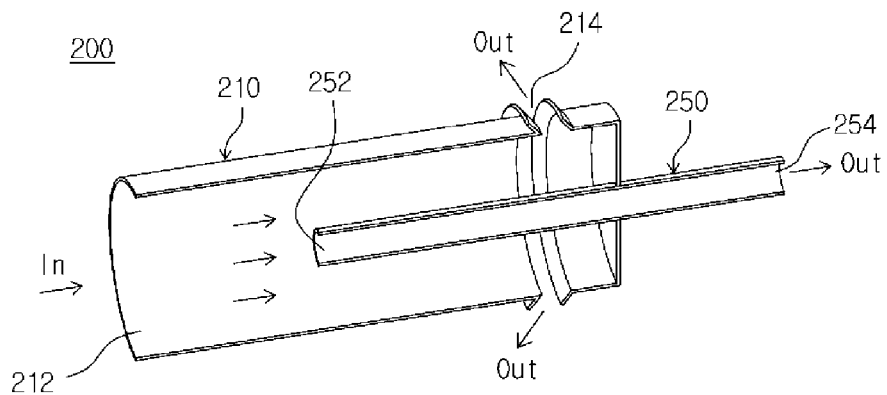
Figure 5:
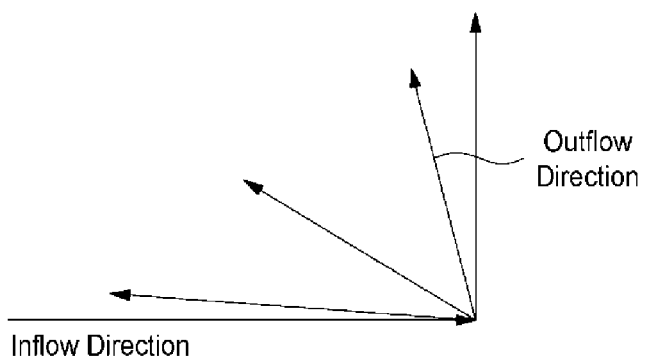
FIG. 5 is a diagram exemplifying a relationship between an inflow direction and an outflow direction of a fluid with respect to a particle sampling probe according to one embodiment of the present disclosure.

FIGS. 4 and 5 are views for explaining a particle sampling probe according to a second embodiment of the present disclosure.

Referring to FIG. 4, the particle sampling probe 200 according to the second embodiment of the present disclosure may include an external duct 210 and a sampling duct 250. Hereinafter, each configuration will be described in detail.

The external duct 210 may extend in the longitudinal direction and may include a first inlet 212 through which an external fluid flows and a first outlet 214 which is provided in an end opposite the first inlet 212.

The first inlet 212 may receive the external fluid to be sampled. A part of the external fluid introduced into the first inlet 212 may be provided to the sampling duct 250 to be described later and the rest of the introduced external fluid may be discharged through the first outlet 214 to be described later.

The first outlet 214 may be located at one side of the external duct 210. The first outlet 214 may be formed in an annular shape in the external duct 210. The first outlet 214 may be formed in the external duct 210 as a hole, or as a shroud as illustrated.

The outflow direction of the first outlet 214 may be formed to be at least partially opposite the inflow direction in which the external fluid is introduced into the first inlet 212. More specifically, the outflow direction of the first outlet 214 may form an acute angle with the inflow direction of the first inlet 212.

Referring to FIG. 5, when the inflow direction is directed rightward (x-axis), the outflow direction may form an acute angle with respect to the x-axis (see the dashed arrow). A hole and/or a shroud constituting the outlet 214 may be provided in an inclined form such that the outflow direction of the first outlet 214 and the inflow direction of the first inlet 212 form an acute angle.

Referring again to FIG. 4, the first outlet 214 may be spaced apart from the first inlet 212 by a distance P in the longitudinal direction. This is to create a pressure difference between the first inlet 212 and the first outlet 214 as described above. Therefore, the particle sampling probe according to the second embodiment of the present disclosure can also automatically provide constant-speed sampling.

The sampling duct 250 may extend in a direction substantially the same as the external duct 210 and may be provided inside the external duct 210. More specifically, the outer wall of the sampling duct 250 may be spaced apart from the inner wall of the external duct 210 by a distance g. Also, the sampling duct 250 may be coaxial with the external duct 210.

The sampling duct 250 may include a second inlet 252 into which the sampling fluid in the external fluid is introduced and a second outlet 254 provided at the end opposite the second inlet.

The second inlet 152 of the sampling duct 250 may be provided with some of the external fluid introduced into the first inlet 212 of the external duct 210 as a sampling fluid. In this case, since the sampling duct 250 is spaced apart from the external duct 210, the second inlet 252 of the sampling duct 250 may be selectively provided with a central fluid, which is insensitive to a change in flow rate, in the external air introduced into the first inlet 212 of the external duct 210.

Meanwhile, the non-sampling fluid which was not able to be introduced into the second inlet 252 of the sampling duct 250 flows through a gap g between the outer wall of the sampling duct 250 and the inner wall of the external duct 210.

The fluid introduced into the second inlet 252 of the sampling duct 250 may be transferred to a measurement instrument through the second outlet 254 provided in the end opposite the second inlet 252. At this time, the end opposite the second inlet 252 may be directly or indirectly connected to the measurement instrument.

In the foregoing, the particle sampling probe according to the second embodiment of the present disclosure has been described.

The particle sampling probe according to the first embodiment of the present disclosure described above provides a flow path of the non-sampling fluid through the discharge passage, whereas the particle sampling probe according to the second embodiment of the present disclosure may provide the non-sampling fluid through a hole or a shroud which is directly formed in the external duct.

Since the operation method of the particle sampling probe according to the second embodiment of the present disclosure corresponds to the operation method of the particle sampling probe according to the first embodiment of the present disclosure described above, the description of the operation method of the particle sampling probe according to the second embodiment of the present disclosure will omitted.

Figure 6:
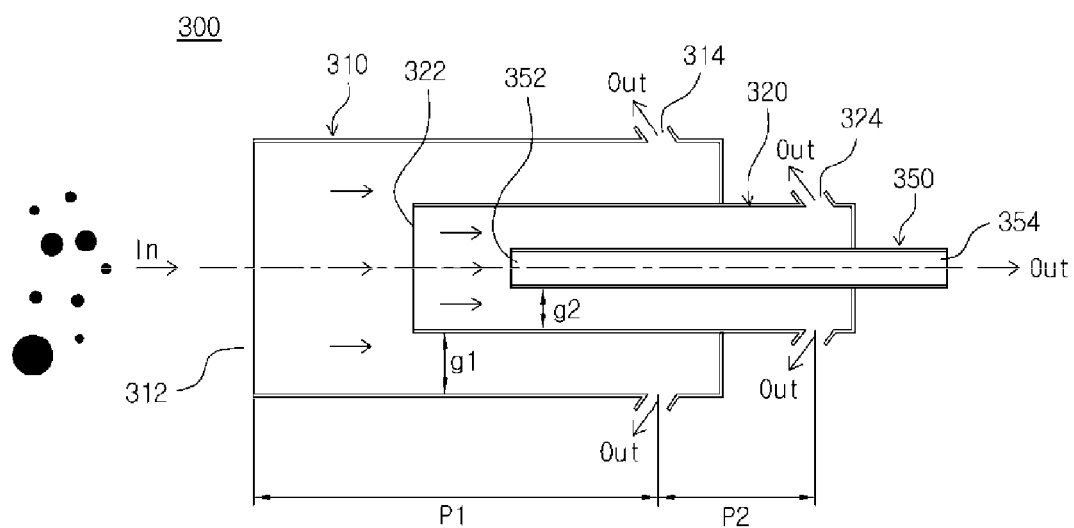
FIG. 6 illustrates a cross-sectional view and a partially cut-away perspective view for explaining a particle sampling probe according to a third embodiment of the present disclosure.
Figure 6:
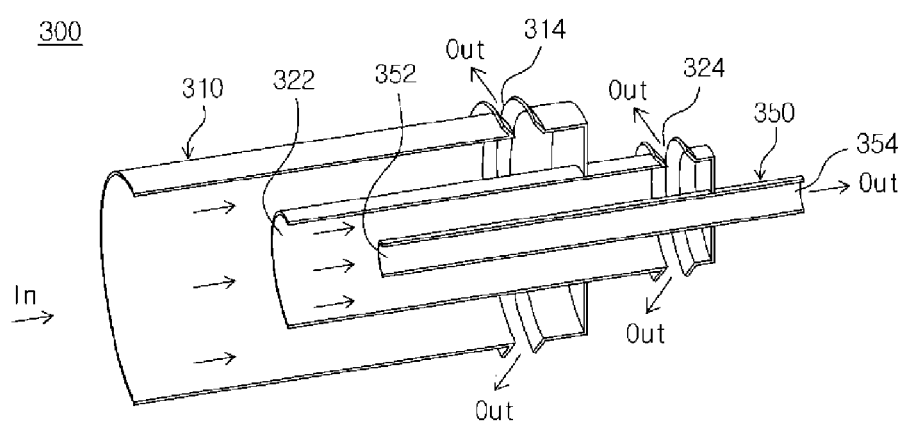

FIG. 6 illustrates a cross-sectional view and a partially cut-away perspective view for explaining a particle sampling probe according to a third embodiment of the present disclosure.

Referring to FIG. 6, the particle sampling probe 300 according to a third embodiment of the present disclosure may include a first external duct 310, a second external duct 320, and a sampling duct 350. Hereinafter, each configuration will be described in detail.

The first external duct 310 may extend in the longitudinal direction and may include a first sub-inlet 312 into which an external fluid is introduced and a first sub-outlet 314 provided in an end opposite the first sub-inlet 312.

The second external duct 320 may extend in the longitudinal direction and may include a second sub-inlet 322 into which an external fluid is introduced and a second sub-outlet 324 provided in an end opposite the second sub-inlet 322.

At this time, the second external duct 320 may be provided inside the first external duct 310. For example, the second external duct 320 may be provided inside the first external duct 310 coaxially with the first external duct 310.

According to one embodiment, the inner wall of the first external duct 310 may be spaced apart from the outer wall of the second external duct 320 by a distance g1. Accordingly, the outermost fluid of the first external duct 310, which is sensitive to a change in the speed of the external air, is discharged through the first sub-outlet 314 of the first external duct 310, and the central fluid of the first external duct 310, which is insensitive to a change in the speed of the external air, may be selectively provided to the second external duct 320.

The outflow directions of the first and second sub-outlets 314 and 324 correspond to the descriptions of those in the above-described embodiment, and thus descriptions thereof will be omitted.

The sampling duct 350 may extend in a direction, which is substantially the same as the first or second external duct 310 or 320, and may include a second inlet 352 and a second outlet 354 provided at the end opposite the second inlet 352.

At this time, the sampling duct 350 may be provided inside the second external duct 320. For example, the sampling duct 350 may be provided inside the second external duct 320 coaxially with the second external duct 320.

According to one embodiment, the inner wall of the second external duct 320 may be spaced apart from the outer wall of the first external duct 310 by a distance g2. Accordingly, a fluid primarily filtered by the first external duct 310 can be secondarily filtered by the second external duct 320.

In the foregoing, the particle sampling probe according to the third embodiment of the present disclosure has been described.

Unlike the above-described embodiments, the particle sampling probe according to the third embodiment provides a plurality of external ducts for multi-stage filtering, thereby enabling constant-speed sampling of the sampling fluid flowing into the sampling duct.

Since the operation method of the particle sampling probe according to the third embodiment of the present disclosure corresponds to the operation method of the particle sampling probe according to the embodiments described above, the description of the operation method of the particle sampling probe according to the third embodiment will omitted.

Figure 7:
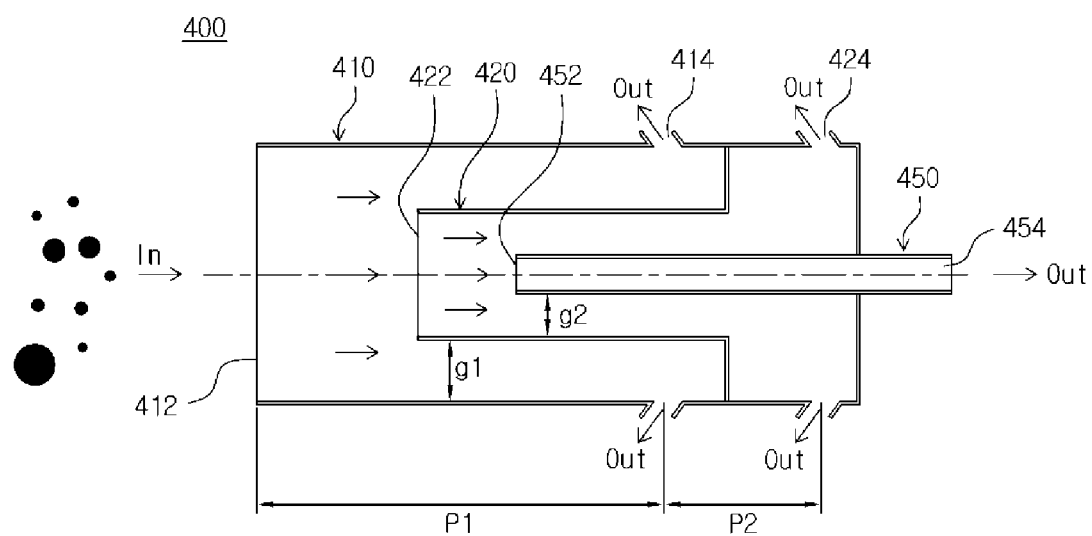
FIG. 7 illustrates a cross-sectional view and a partially cut-away perspective view for explaining a particle sampling probe according to a fourth embodiment of the present disclosure.
Figure 7:
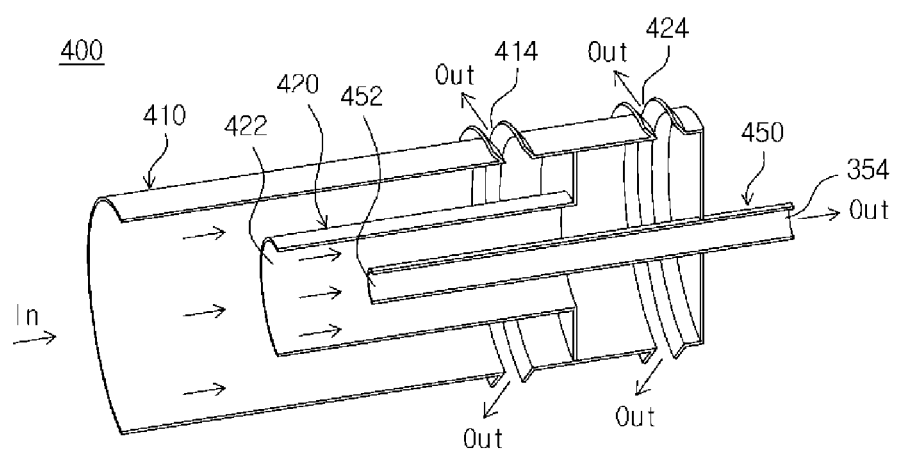

FIG. 7 illustrates a cross-sectional view and a partially cut-away perspective view for explaining a particle sampling probe according to a fourth embodiment of the present disclosure.

Referring to FIG. 7, the particle sampling probe 400 according to a fourth embodiment of the present disclosure may include a first external duct 410, a second external duct 420, and a sampling duct 450. Hereinafter, each configuration will be described in detail.

The first external duct 410 may extend in the longitudinal direction and may include a first sub-inlet 412 into which an external fluid is introduced and a first sub-outlet 414 provided in an end opposite the first sub-inlet 412.

The second external duct 420 may extend in the longitudinal direction and may include a second sub-inlet 422 into which an external fluid is introduced and a first sub-outlet 424 provided in an end opposite the second sub-inlet 422.

At this time, the second external duct 420 may be provided inside the first external duct 410. For example, the second external duct 420 may be provided inside the first external duct 410 coaxially with the first external duct 410.

According to one embodiment, the second external duct 420 extends in the longitudinal direction, and the outer diameter of the second external duct 420 may be larger in the second sub-outlet 424 than in the second sub-inlet 422. Accordingly, the outer wall of the second external duct 420 may form a stream line continuous with the outer wall of the first external duct 410. In another point of view, the external fluid may flow continuously from the first external duct 410 to the second external duct 420. At this time, the outer wall of the second external duct 420 may form a stream line which is the same as the outer wall of the first external duct 410.

As a result, a pressure profile may be continuously changed from the first sub-inlet 412 of the first external duct 410 to the first sub-outlet 414 of the first external duct 410 and from the first sub-outlet 414 of the first external duct 410 to the second sub-outlet 424 of the second external duct 420.

The outflow directions of the first and second sub-outlets 414 and 424 correspond to the those described in connection with the above-described embodiment, and thus descriptions thereof will be omitted.

The sampling duct 450 may extend in a direction, which is substantially the same as the first or second external duct 410 or 420, and may include a second inlet 452 and a second outlet 454 provided at the end opposite the second inlet 452.

At this time, the sampling duct 450 may be provided inside the second external duct 420. For example, the sampling duct 450 may be provided inside the second external duct 420 coaxially with the second external duct 420.

According to one embodiment, the outer wall of the second external duct 420 may be spaced apart from the inner wall of the first external duct 410 by a distance g1, and the outer wall of the sampling duct 450 may be spaced apart from the inner wall of the second external duct 420 by a distance g2. Accordingly, a center fluid, which is insensitive to a speed change in the external flow rate, may be provided to the entire sampling duct 450.

In the foregoing, the particle sampling probe according to the fourth embodiment of the present disclosure has been described.

Unlike the embodiments described above, the particle sampling probe according to the fourth embodiment provides a plurality of external ducts, and it is possible to achieve a constant-speed sampling of the sampling fluid by providing stream lines through a plurality of outlets provided in the plurality of external ducts.

Since the operation method of the particle sampling probe according to the fourth embodiment of the present disclosure corresponds to the operation method of the particle sampling probe according to the embodiments described above, the description of the operation method of the particle sampling probe according to the fourth embodiment will omitted.

Figure 8:
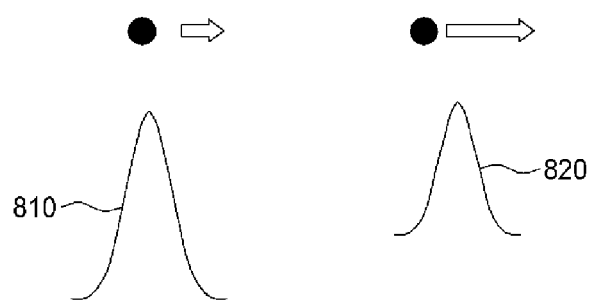
FIG. 8 is a diagram exemplifying a shape of a pulse generated according to a speed of a fine dust particle in a number concentration measuring sensor of a fine dust measuring device according to an embodiment of the present disclosure.

FIG. 8 is a diagram exemplifying shapes of pulses generated according to a speed of a fine dust particle in a number concentration measuring sensor of a fine dust measuring device according to an embodiment of the present disclosure.

The first number concentration measuring sensor 40 and the second number concentration measuring sensor 50 of the fine dust measuring device 5, which have been described above with reference to FIG. 8, are sensors that use an optical measuring method, and determine whether or not particles pass depending on whether or not the height of a pulse generated according to the amount of laser beams incident on photodiodes provided in the sensors is equal to or greater than a specified threshold value when fine dust particles pass through the region to which the laser beams are projected.

Referring to FIG. 8, as indicated by 810, the first number concentration measuring sensor 40 and the second number concentration measuring sensor 50 may be configured to generate a pulse, the height of which is formed to be a specified threshold value or more when the fine dust particles move at a relatively low speed. However, as indicated by 820, the first number concentration measuring sensor 40 and the second number concentration measuring sensor 50 may be configured not to generate a pulse, the height of which is formed to be a specified threshold value or more when the fine dust particles move at a relatively high speed. That is, in order for the first number concentration sensor 40 and the second number concentration sensor 50 to generate a pulse having a height equal to or higher than the threshold value, the time for the particles to stay in a region where the laser beams are projected needs to be longer than a specified time. That is, when the moving speed of the fine dust particles increases, there is a high possibility that errors occur in the measurement of the number concentration of particles.

Therefore, the flow rate control pump 60 of the fine dust measuring device 5 according to one embodiment of the present disclosure controls the volume flow rate per unit time of the fluid introduced from the particle sampling probe 10 to be a predetermined numerical value. That is, the flow rate control pump 60 keeps the volume flow rate per unit time of the fluid, which is introduced into the fine dust measuring device 5 through the particle sampling probe 10, constant, so that it is possible to prevent the speed of the fine dust particles introduced into the first number concentration measuring sensor 40 and the second number concentration measuring sensor 50 from increasing.

At this time, the flow rate control pump 60 may include a pump implemented in any one of a piston type, a roots type, and a vane type.

Figure 9:
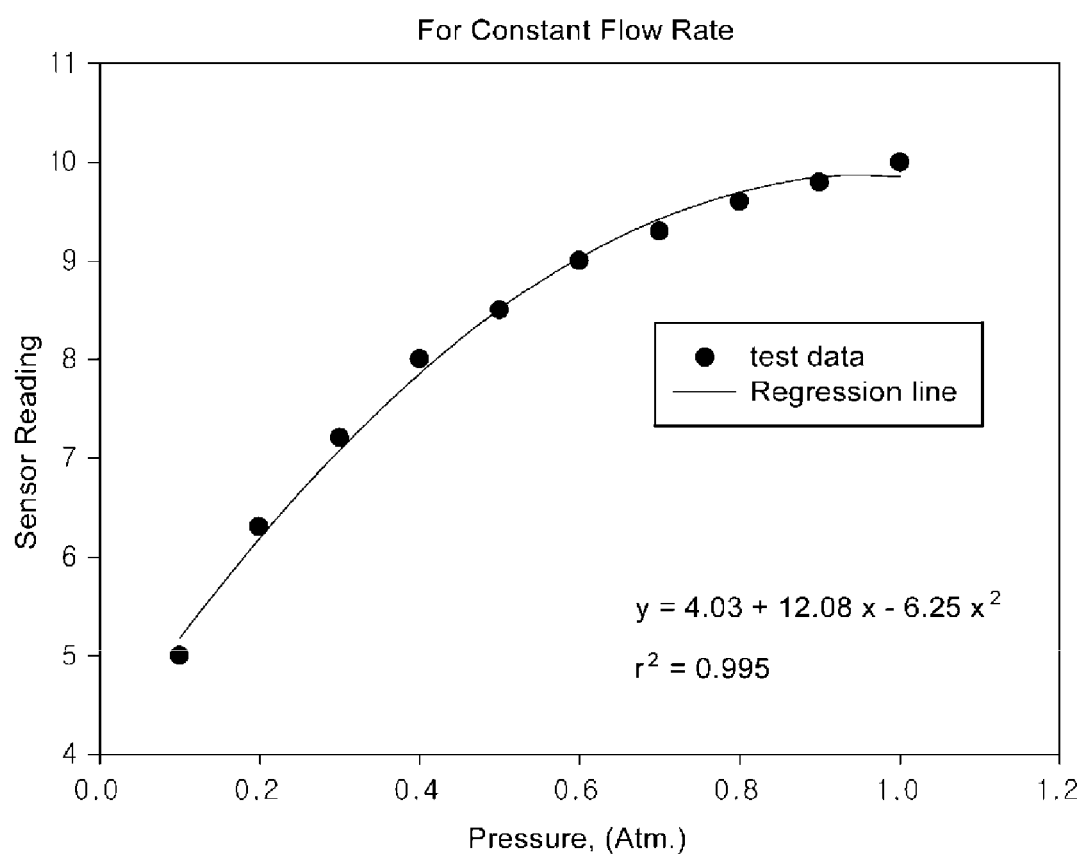
FIG. 9 is a diagram exemplifying an atmospheric pressure-sensor value graph used by a flow control pump of a fine dust measurement apparatus according to an embodiment of the present disclosure in order to maintain a volume flow rate to be constant.

FIG. 9 is a diagram exemplifying an atmospheric pressure-sensor value graph used by a flow control pump of a fine dust measurement apparatus according to an embodiment of the present disclosure in order to maintain a volume flow rate to be constant.

Referring to FIG. 9, when a graph is drawn by correlating sensor values received from the flow rate control sensor 62 with the air pressures measured through the atmospheric pressure sensor 64 provided outside the fine dust measuring device 5, a graph can be derived as in FIG. 9.

Figure 10:
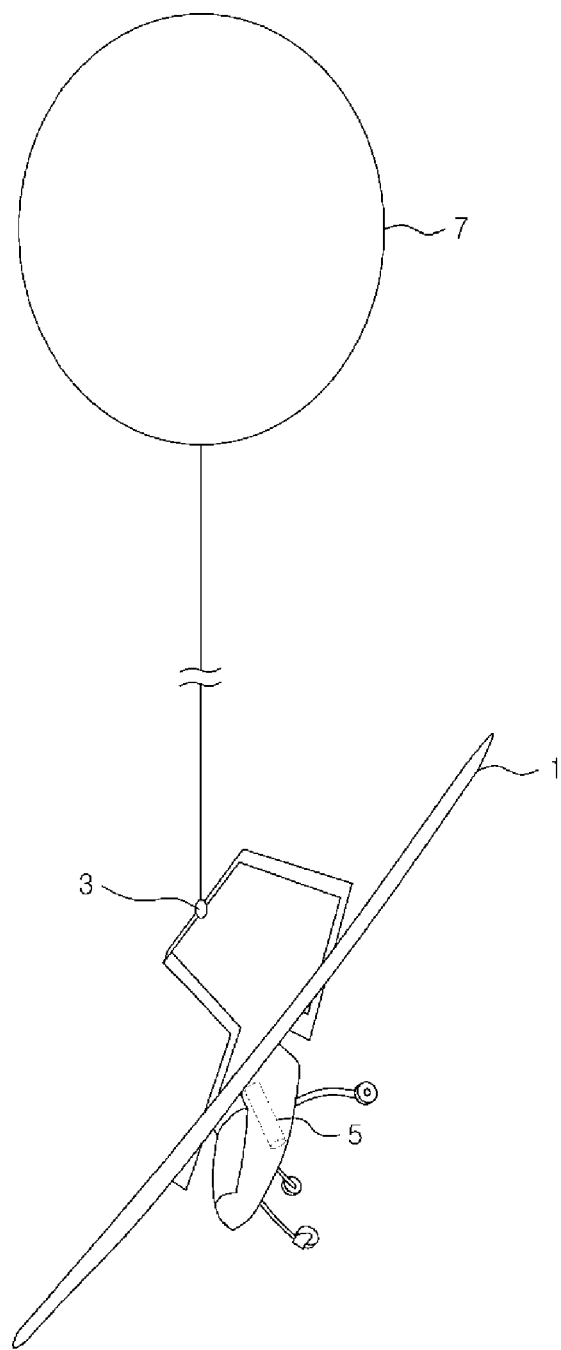
FIG. 10 is a diagram exemplifying a fine dust measuring device according to an embodiment of the present disclosure.

The memory 72 may store in advance flow control information, which is information indicating the relationship between the sensor values and the external atmospheric pressures as shown in the graph of FIG. 9. At this time, the flow rate control information may include an equation for deriving the graph as shown in FIG. 10, or table information for matching and storing the sensor values and the atmospheric pressures. The processor 70 refers to the flow rate control information stored in the memory 72 in order to check the target sensor value which is the sensor value corresponding to the current atmospheric pressure measured through the atmospheric pressure sensor, and controls the flow rate control pump 60 such that the target sensor value is equal to the sensor value output through a differential pressure sensor or a mass flow rate sensor. Accordingly, it is possible to control the volume flow rate per unit time of the fluid introduced through the particle sampling probe 10 to be constant even when the external atmospheric pressure varies according to the movement of the fine dust measuring device according to one embodiment of the present disclosure.

Therefore, with the fine dust measuring device 5 according to one embodiment of the present disclosure, the measurement accuracy of fine dust particles can be maintained through the optical measuring method by making the volume flow rate of the sampling fluid introduced through the particle sampling probe 10 constant even in an environment having an extremely low atmospheric pressure such as a high-altitude environment.

FIG. 10 is a diagram exemplifying a fine dust measuring device according to an embodiment of the present disclosure.

Referring to FIG. 10, a fine dust measuring device according to an embodiment of the present disclosure includes a flight vehicle 1, a balloon connecting unit 3, and a fine dust measuring unit 5.

The flight vehicle 1 moves in accordance with a control signal received from a controller (not illustrated) on the ground or a predetermined program on a high altitude in the form of a drone. The moving principle and the control process, etc. of the flight vehicle 1 are based on known unmanned plane technology, and a detailed description thereof will be omitted.

The balloon connecting unit 3 connects one end of the flight vehicle 1 and the balloon 7 and may be electrically connected to the flight vehicle 1 so as to receive a separation request signal that requests separation of the flight vehicle 1 and the balloon 7 from each other. At this time, the flight vehicle 1 may transmit a separation request signal to the balloon connecting unit 3 in accordance with a control signal received from a controller or a predetermined program.

After the flight vehicle 1 and the balloon 7 are separated from each other, the flight vehicle 1 may start the flight according to the control signal received from the controller or the program.

The fine dust measuring unit 5 is attached to the inside or outside of the flight vehicle 1 to suction air around the flight vehicle and to measure the concentration of fine dusts contained in the suctioned air.

Figure 11:
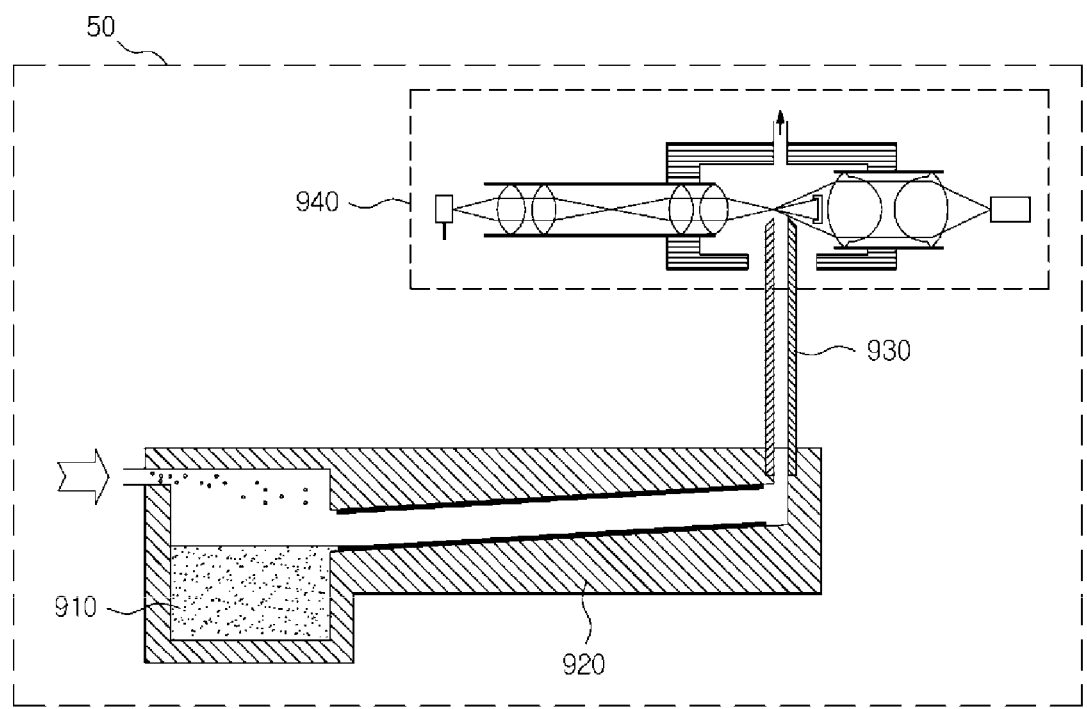
FIG. 11 is a diagram exemplifying a structure of a second number concentration measuring sensor included in a fine dust measuring unit of the fine dust measuring device according to an embodiment of the present disclosure.

FIG. 11 is a diagram exemplifying a structure of a second number concentration measuring sensor included in a fine dust measuring unit of the fine dust measuring device according to an embodiment of the present disclosure.

Referring to FIG. 11, the second number concentration measuring sensor 50 includes a solvent tank 910, a saturator 920, a condenser 930, and a sensing unit 940.

The solvent tank 910 stores a volatile solvent and causes the volatile solvent to flow into the saturator 920 in a predetermined amount per unit time.

The saturator 920 receives the sampling fluid introduced via the particle sampling probe 10, mixes the gas, which is volatilized from the volatile solvent, with the sampling fluid to produce a mixed gas, and introduces the mixed gas into the condenser 930. The saturator 920 includes a flow path configured to allow the sampled fluid to flow therein, and a heater configured to maintain the internal temperature of the flow path at a predetermined temperature. At this time, the flow path of the saturator 920 may be formed of a porous material, and the volatile solvent introduced from the solvent tank 910 may flow into the porous material to evaporate.

The condenser 930 receives and condenses the mixed gas introduced from the saturator 920, and introduces the condensed mixed gas into the sensing unit 940. The condenser 930 may include a flow path configured to allow the mixed gas to flow from the saturator 920 to the sensing unit 940 and a heat radiation source (e.g., a heat radiation fan, a heat radiation fin, or the like) configured to lower the temperature in the flow path to a predetermined temperature. Thus, the volatile solvent can condense on the fine dusts of the fluid contained in the mixed gas.

The sensing unit 940 senses the fine dusts on which the volatile solvent is condensed and measures the number concentration of the fine dusts in the sampled fluid. The sensing unit 940 includes a light-emitting source and a light-sensing sensor, measures a scattering degree of light projected from the light-emitting source through the light-sensing sensor, and calculates the number concentration of the fine dusts depending on the scattering degree.

At this time, the above-mentioned second number concentration measuring sensor 50 may be implemented such that the shape of each functional unit is changed to be different from that of FIG. 11 according to the implementation method thereof.

The second number concentration measuring sensor 50 described above with reference to FIG. 11 is configured such that the flow direction of the mixed gas (hereinafter, referred to as a "mixed gas inflow direction") introduced from the condenser 930 into the sensing unit 940 is formed in a direction other than a horizontal direction. Thus, the volatile solvent that has not been volatilized in the condenser 930 is not introduced into the sensing unit 940 through the condenser 930. The sensing unit 940 is a module configured to measure the light scattering degree. Thus, when the volatile solvent in the liquid state is introduced, the sensing unit 940 malfunctions, and thus cannot accurately measure the number concentration of fine dusts. However, when the mixed gas inflow direction of the second number concentration measuring sensor 50 is set to be perpendicular to the axial direction which is the forward direction of the flight vehicle 1, the volatile solvent of the second number concentration measuring sensor 50 may be introduced into the sensing unit 940 while the flight vehicle 1 connected vertically to the balloon 7 is moving.

Figure 12:
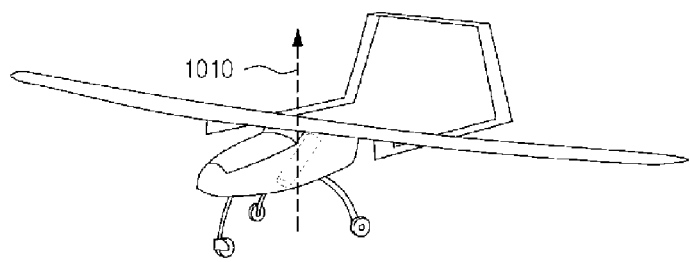
FIG. 12 is a diagram exemplifying a mixed gas inflow direction for a second number concentration measuring sensor while the fine dust measuring device according to an embodiment of the present disclosure horizontally flies and while the fine dust measuring device is connected to a balloon and increases in altitude.
Figure 12:
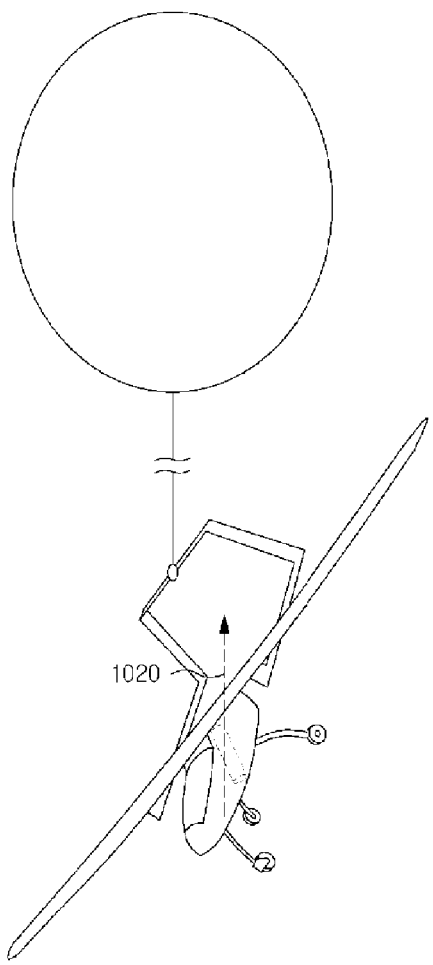
Figure 13:
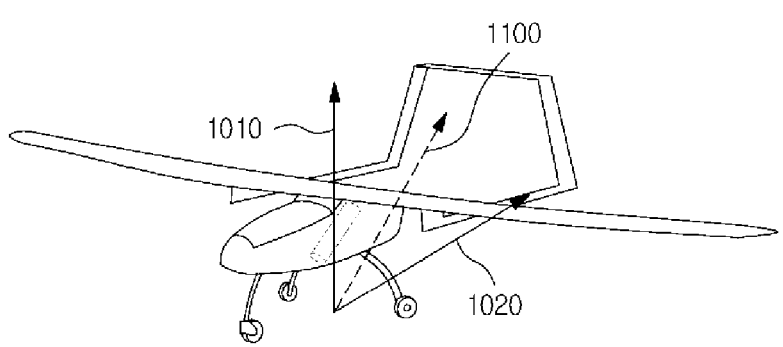
FIG. 13 is a diagram exemplifying an anti-gravity direction in horizontal flight, and an anti-gravity in balloon flight, and a mixed gas inflow direction with reference to a based on a flight vehicle of the fine dust measuring device according to an embodiment of the present disclosure.
Figure 14:
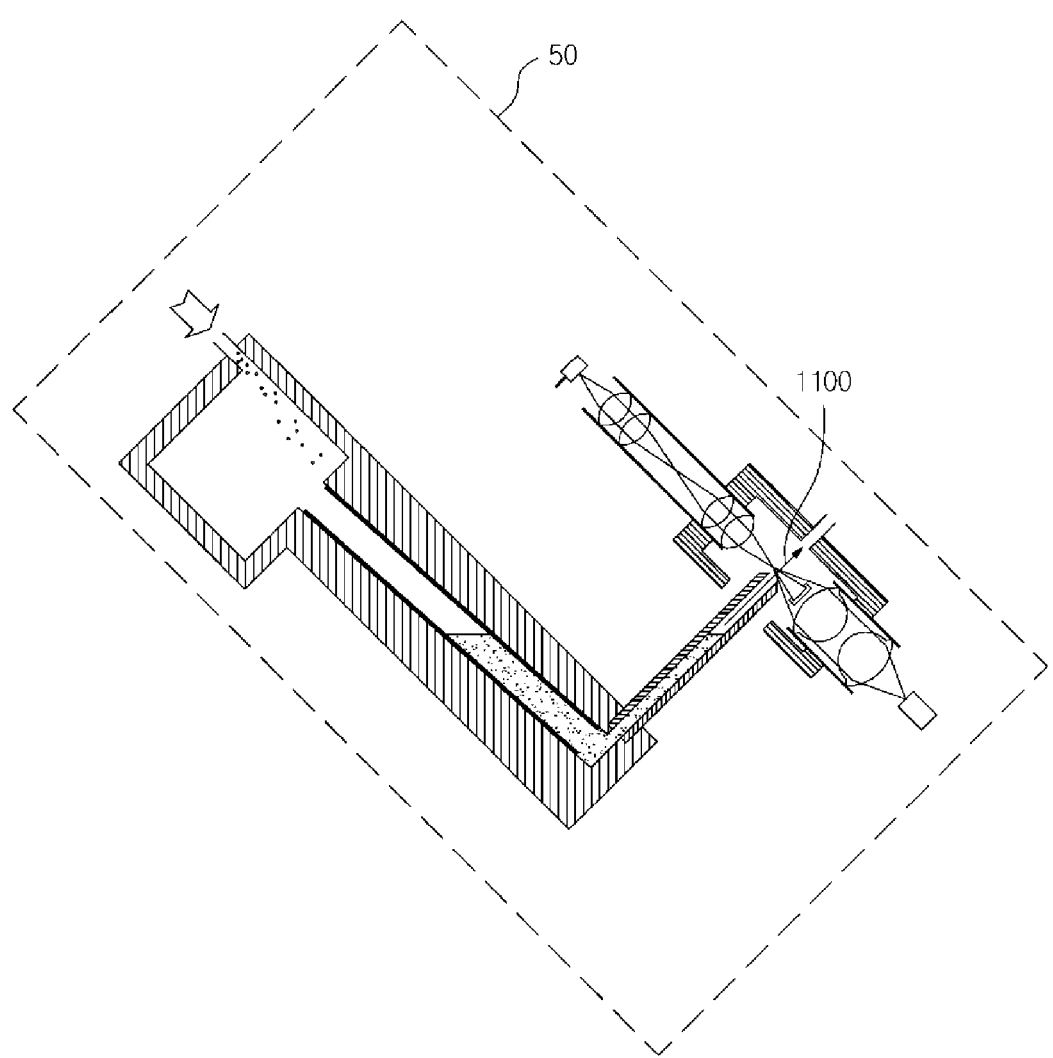
FIG. 14 is a diagram exemplifying a volatile solvent in a second number concentration measuring sensor when the fine dust measuring device according to an embodiment of the present disclosure is connected to a balloon and increases in altitude.

FIG. 12 is a diagram exemplifying a mixed gas inflow direction for a second number concentration measuring sensor while the fine dust measuring device according to an embodiment of the present disclosure horizontally flies and while the fine dust measuring device is connected to a balloon and raises the altitude, FIG. 13 is a diagram exemplifying an anti-gravity direction in horizontal flight, and an anti-gravity in balloon flight, and a mixed gas inflow direction with reference to a based on a flight vehicle of the fine dust measuring device according to an embodiment of the present disclosure, and FIG. 14 is a diagram exemplifying a volatile solvent in a second number concentration measuring sensor when the fine dust measuring device according to an embodiment of the present disclosure is connected to a balloon and increases in altitude.

Referring to FIG. 12, the second number concentration sensor 50 of the fine dust measuring device according to the embodiment of the present disclosure may be mounted inside or outside the flight vehicle such that the mixed gas inflow direction corresponds to a direction between the direction opposite the gravitational force, which is applied to the flight vehicle 1 which is horizontally flying (hereinafter, referred to as a "horizontal flight anti-gravity direction 1010") and the direction opposite the gravitational force, which is applied to the flight vehicle 1 which is connected to the balloon and is increasing in altitude (hereinafter, referred to as a "balloon flight anti-gravity direction 1020").

Referring to FIG. 13, the fine dust measuring unit 5 may be attached inside or outside the flight vehicle 1 such that the angle between the horizontal flight anti-gravity direction 1010 and the balloon flight anti-gravity direction 1020 may be formed to be 90 degrees or less, and the mixed gas inflow direction may be formed in a direction 1100 between the horizontal flight anti-gravity direction 1010 and the balloon flight anti-gravity direction 1020.

Referring to FIG. 14, since the mixed gas inflow direction of the fine dust measuring device does not correspond to the horizontal direction even when the flight vehicle 1 is tilted and connected to the balloon to increases in altitude, it is possible to prevent the liquid-phase volatile solvent from flowing into the sensing unit 940. Therefore, the fine dust measuring device according to one embodiment of the present disclosure can prevent an error from occurring in the number concentration measured through the second number concentration measuring sensor 50 after the volatile solvent flows into the sensing unit 940.

Figure 15:
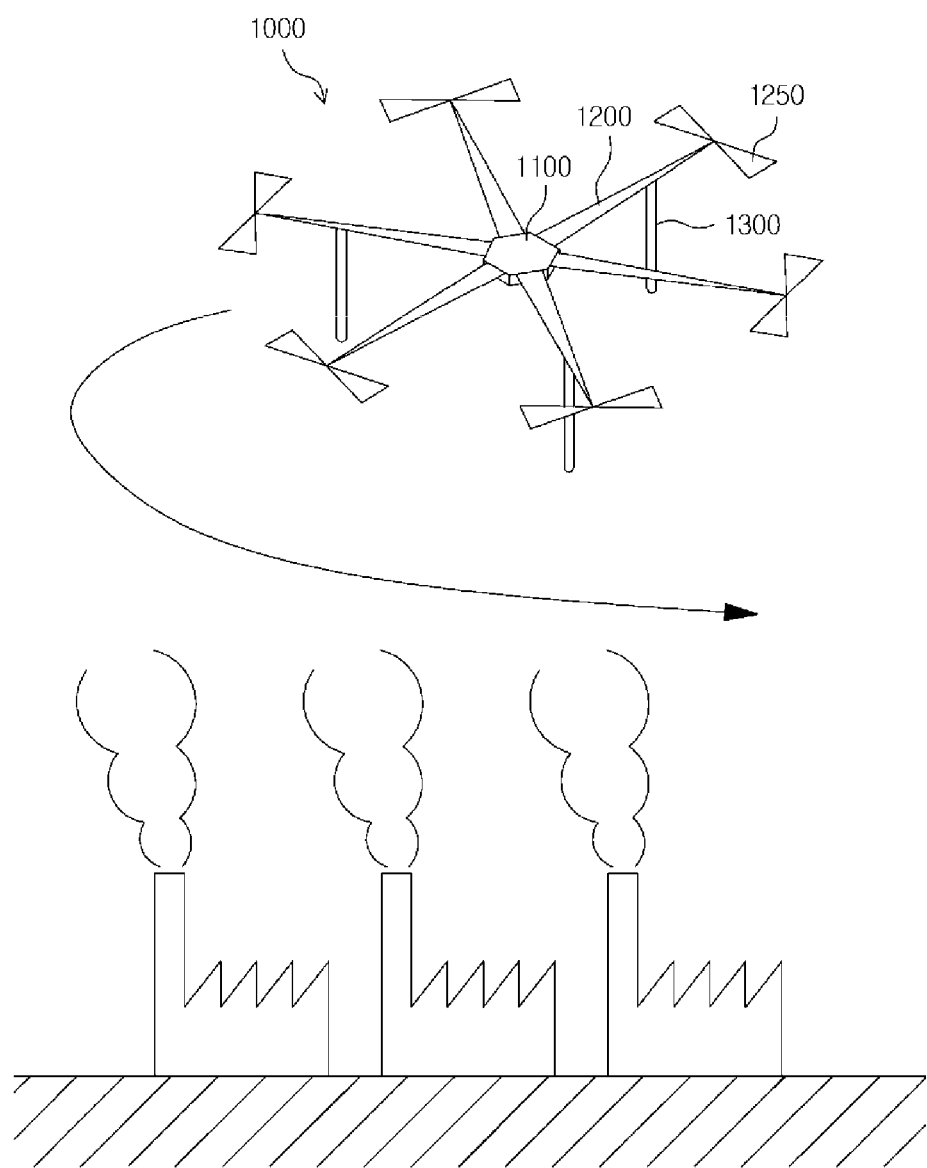
FIG. 15 is a diagram exemplifying an unmanned observation plane equipped with a fine dust measuring device according to one embodiment of the present disclosure.

FIG. 15 illustrates an unmanned observation plane equipped with a fine dust measuring device according to one embodiment of the present disclosure.

The fine dust measuring device according to one embodiment of the present disclosure may be mounted on an unmanned observation plane, for example, a drone, so as to sense harmful particles in the atmosphere. Through this, the flow path of the harmful particles and/or the amount of the harmful particles can be calculated.

Referring to FIG. 15, the unmanned observation plane 1000 may include at least one of a body portion 1100, a frame 1200, a propeller 1250, and a leg 1300.

The body portion 1100 may be formed in the center of the unmanned observation plane 1000. At this time, a fine dust measuring device including a particle sampling probe according to embodiments of the present disclosure described above may be mounted on the body portion 1100. At this time, the direction in which the first inlet 212 of the particle sampling probe is directed may be set to the forward direction of the unmanned observation plane 1000.

In addition, the body portion 1100 may further include a communication unit. The communication unit may provide a signal from the particle sampling probe to an operator.

The frame 1200 may extend in the radial direction from the body portion 1100 to provide a structure for connecting the body portion 1100 and the propeller 1250. As illustrated, for example, six frames 1200 may be provided.

Legs 1300 may extend downward from one sides of the frames 1200, respectively. The unmanned observation plane 1000 can maintain balance while landing using the legs 1300.

The propeller 1250 may be provided at one end of each frame 1200 so as to provide lift to the unmanned observation plane 1000 so that the unmanned observation plane 1000 can fly.

While the present disclosure has been described in detail with reference to exemplary embodiments thereof, the scope of the present disclosure is not limited to the disclosed exemplary embodiments and should be interpreted based on the accompanying claims. A person skilled in the art will appreciate that many modifications and variations can be made without departing from the scope of the present disclosure.

The invention claimed is:

1. A particle sampling probe comprising:
    an external duct defining a first inlet and a first outlet at an end of the external duct that is opposite to the first inlet, the external duct including:
        a first portion extending in a longitudinal direction and defining the first inlet into which an external fluid is introduced into the external duct, the first portion is completely surrounded by the first outlet, the first outlet is partially defined by the first portion and spaced apart from the first inlet in a longitudinal direction;
        a second portion extending directly from the first portion at a right angle; and
        a third portion extending directly from the second portion at a right angle towards the first outlet, the third portion completely surrounds the first portion, the third portion is a discharge passage through which a non-sampling fluid in the external fluid flows in a direction that is opposite to flow of the external fluid through the first portion; and
    a sampling duct extending in the longitudinal direction inside the first portion of the external duct, the sampling duct defining a second inlet into which a sampling fluid in the external fluid is introduced, and a second outlet provided at an end of the sampling duct opposite the second inlet, both the first portion and the third portion of the external duct completely surround the sampling duct, a gap through which the non-sampling fluid flows is defined between the sampling duct and the first portion of the external duct, the sampling fluid flows through the sampling duct in a direction that is opposite to flow of the non-sampling fluid through the discharge passage of the third portion;
    wherein an outflow direction of the first outlet is formed to be at least partially opposite an inflow direction in which the external fluid is introduced into the first inlet.

2. The particle sampling probe of claim 1, wherein the sampling duct and the external duct are coaxial to each other.

3. A particle sampling probe comprising:
    a first external duct extending in a longitudinal direction and comprising a first sub-inlet into which an external fluid is introduced and a first sub-outlet provided at an end opposite the first sub-inlet;
    a second external duct extending in a longitudinal direction inside the first external duct and comprising a second sub-inlet into which a part of the external fluid is introduced and a second sub-outlet provided at an end opposite the second sub-inlet; and
    a sampling duct extending in the longitudinal direction inside the second external duct and comprising a second inlet into which a sampling fluid in the fluid introduced into the second sub-inlet is introduced, and a second outlet provided at an end opposite the second inlet,
    wherein an outflow direction of the first and second-sub outlets is formed to be at least partially opposite an inflow direction in which the external fluid is introduced into the first sub-inlet.

4. The particle sampling probe of claim 3, wherein the outflow direction of the first and second sub-outlets forms an acute angle with the inflow direction in which the external fluid is introduced into the first sub-inlet, and the first sub-outlet is formed in the first external duct to be spaced apart from the first sub-inlet in the longitudinal direction, and the second sub-outlet is formed in the second external duct to be spaced apart from the second sub-inlet in the longitudinal direction.

5. The particle sampling probe of claim 3, wherein an outer wall of the first external duct and an outer wall of the second external duct provide a continuous stream line for the external fluid.

6. The particle sampling probe of claim 3, wherein an outer wall of the first external duct and an outer wall of the second external duct provide a discontinuous stream line for the external fluid.

* * * * *